United States Patent [19]
Briving et al.

[11] Patent Number: 5,106,862
[45] Date of Patent: Apr. 21, 1992

[54] DERIVATIVES OF BENZIMIDAZOLES ACTIVE AS ANTI-ULCER AGENTS

[75] Inventors: Carin B. Briving, Billdal; Stig A. I. Carlsson, Mölnlycke; Per L. Lindberg; Annie H. Mattsson, both of Askim; Mats P. Nordberg, Gothenburg; Björn M. G. Wallmark, Mölnlycke, all of Sweden

[73] Assignee: Aktiebolaget Hassle, Molndal, Sweden

[21] Appl. No.: 631,221

[22] Filed: Dec. 12, 1990

Related U.S. Application Data

[63] Continuation of Ser. No. 113,459, Oct. 26, 1987, abandoned.

[30] Foreign Application Priority Data

Oct. 27, 1986 [SE] Sweden .................. 8604566

[51] Int. Cl.⁵ .................. A61K 31/415; C07D 235/04
[52] U.S. Cl. .................. 514/394; 548/325
[58] Field of Search .................. 548/325; 514/394

[56] References Cited

U.S. PATENT DOCUMENTS

| | | | |
|---|---|---|---|
| 4,182,766 | 1/1980 | Krassó et al. | 548/325 |
| 4,435,406 | 3/1984 | Krasso et al. | 548/325 |
| 4,599,347 | 7/1986 | Krasso et al. | 548/325 |

FOREIGN PATENT DOCUMENTS

| | | | |
|---|---|---|---|
| 0005129 | 10/1979 | European Pat. Off. | 548/325 |
| 0045200 | 2/1982 | European Pat. Off. | 548/325 |
| 0111993 | 6/1984 | European Pat. Off. | 548/325 |
| 0172631 | 2/1986 | European Pat. Off. | 548/325 |
| 0178413 | 4/1986 | European Pat. Off. | 548/325 |
| 2505913 | 2/1975 | Fed. Rep. of Germany | 548/325 |
| 2737630 | 8/1977 | Fed. Rep. of Germany | 548/325 |
| 0024419 | 11/1967 | Japan | 548/325 |
| 346321 | 9/1968 | Sweden | 548/325 |

OTHER PUBLICATIONS

Arch. Pharm., vol. 229, p. 193, (1966).

*Primary Examiner*—Johann Richter
*Attorney, Agent, or Firm*—White & Case

[57] ABSTRACT

Novel compounds of the general formula I

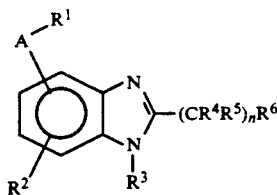

processes for its preparation, pharmaceutical compositions containing such compounds as the active ingredient and the use of the compounds in medicine.

7 Claims, No Drawings

DERIVATIVES OF BENZIMIDAZOLES ACTIVE AS ANTI-ULCER AGENTS

This application is a continuation of application Ser. No. 113,459, filed on Oct. 26, 1987, now abandoned.

DESCRIPTION

1. Field of the Invention

The object of the present invention is to provide novel compounds, and therapeutically acceptable salts thereof, which inhibit exogenously or endogenously stimulated gastric acid secretion and are thus useful as anti-ulcer agents. The compounds also provide gastrointestinal cytoprotective effects and can be used in the prevention of peptic ulcer. The new compounds are more short acting than compounds prior known.

The present invention relates to the use of the compounds of the invention or therapeutically acceptable salts thereof, for inhibiting gastric acid secretion as well as providing gastrointestinal cytoprotective effects in mammals and man. In a more general sense, the compounds of the invention may be used for prevention and treatment of gastrointestinal inflammatory diseases in mammals and man, including e.g. gastritis, gastric ulcer, and duodenal ulcer. Furthermore, the compounds may be used for prevention and treatment of other gastrointestinal disorders, where cytoprotective and/or gastric antisecretory effect is desirable e.g. in patients with gastrinomas, in patients with acute upper gastrointestinal bleeding, and in patients with a history of chronic and excessive ethanol consumption. The invention also relates to pharmaceutical compositions containing at least one compound of the invention, or a therapeutically acceptable salt thereof, as active ingredient. In a further aspect, the invention relates to processes to preparation of such new compounds.

2. Prior Art

Benzimidazole derivatives intended for inhibiting gastric acid secretion are disclosed in the British patent specifications 1 500 043 and 1 525 958, in the U.S. Pat. No. 4,182,766, in the European patent specification 0 005 129, and in the Belgian patent specification 890 024. Benzimidazole derivatives proposed for use in the treatment of prevention of special gastrointestinal inflammatory disease are disclosed in the European patent application with publication no. 0 045 200. The compounds disclaimed in the definition of the compounds with the general formula I are described as intermediates in European patent application 178 413. The last mentioned, European patent application describes also other similar compounds for use in the treatment of inflammatory conditions, e.g. rheumatism and arthritis.

THE INVENTION

It has been found that compounds of the general formula I

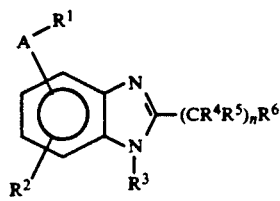

or a pharmaceutically acceptable salt or solvate thereof, in which $R^1$ represents a substituted or unsubstituted aryl or cykloalkyl group with 3-8 carbon atoms in the unsubstituted cyclic group; or an adamantyl group;

$R^2$ represents hydrogen, a lower alkyl, a lower alkoxy or halogen;

$R^3$ represents hydrogen, a lower alkyl, a phenylalkyl with 1-4 carbon atoms in the alkyl group or a cycloalkyl-alkyl group with 3-8 carbon atoms in the cyclic group and 1-4 carbon atoms in the alkyl group;

n is an integer 0-6

$R^4$ represents hydrogen or a lower alkyl;

$R^5$ represents hydrogen or a lower alkyl;

$R^6$ represents hydrogen, a lower alkyl, a substituted or unsubstituted aryl group or when n is 1-6 a hydroxyl group; or when n is 0 an amino, an alkylamino, or a dialkylamino group with 1-4 carbon atoms in the alkyl groups;

A represents an alkylene, optionally connected to, or interrupted by an optionally substituted hetero atom selected from O, S, and NR, wherein R is hydrogen or a lower alkyl, a phenylalkyl with 1-4 carbon atoms in the alkyl group or a cykloalkyl-alkyl group with 3-8 carbon atoms in the cyclic group and 1-4 carbon atoms in the alkyl group; or alkenylene useful in inhibiting gastric acid secretion, as gastrointestinal cytoprotecting agents and in the treatment of gastrointestinal inflammatory diseases in mammals and man.

When used herein in connection with alkyl or alkoxy groups, the term lower means that the group contains up to 6 carbon atoms, preferably up to 4 carbon atoms. The alkyl radicals may have straight or branched chains, and are for example methyl, ethyl, n-propyl, isopropyl, n-butyl, isobutyl, sec.butyl or tert-butyl. Halogen is preferably chloro, bromo or fluoro.

$R^1$ and $R^6$ representing aryl, are preferably a carbocyclic group, suitably of the formula II

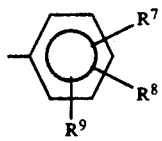

in which each of $R^7$, $R^8$, $R^9$ independently represents hydrogen, a lower alkyl having up to 6 carbon atoms, e.g. methyl, a lower alkoxy having up to 6 carbon atoms, e.g. methoxy, or halogen preferably chloro or fluoro. Alternatively $R^1$ and/or $R^6$ may represent a heterocyclic aryl group, suitably

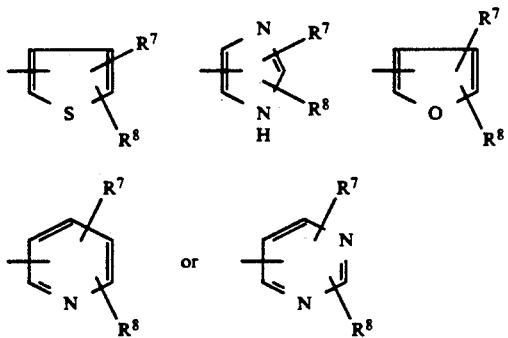

in which $R^7$ and $R^8$ have the meanings given above.

A representing an alkylene, optionally connected to, or interrupted by an optionally substituted hetero atom has preferably up to 6 carbon atoms.

According to the invention, A may represent any of the following i) —(CH$_2$)$_m$—, wherein m is 1-6
ii) —X—(CH$_2$)$_m$—, wherein m is as defined above and X is O, S and NR, wherein R is as defined above
iii) —(CH$_2$)$_x$—X(CH$_2$)$_y$—, wherein x and y are integers with a sum of 1-6 and X is as defined above or
iv) alkenylene with up to 2-6 carbon atoms. Examples of alkenylene groups are —CH=CH— and —CH$_2$—CH=CH—.

The following compounds are excluded from the scope of this application.

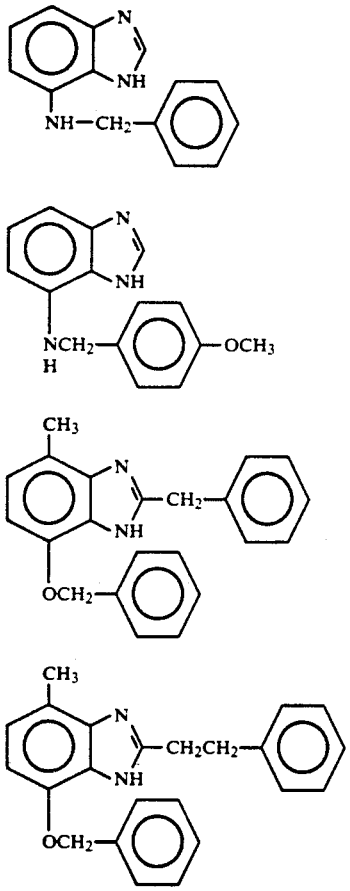

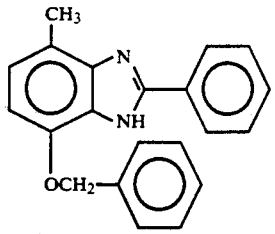

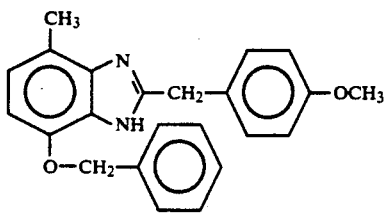

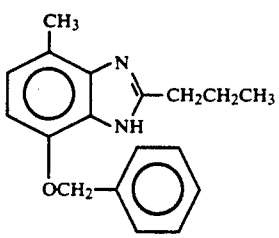

Both the pure enantiomers, racemic mixtures and unequal mixtures of the two enantiomers are within the scope of the present invention. It should be understood that all the diastereomeric forms possible (pure enantiomers or racemic mixtures) are within the scope of the invention.

Especially preferred groups of R$^1$ according to the invention are

R$^1$ representing phenyl, 2'-F-phenyl, 3'-F-phenyl, 4'-F-phenyl, 4'-Cl-phenyl, 2',4'-di-F-phenyl, 2',4'-di-Cl-phenyl and thienyl-2. Especially preferred groups of R$^2$, R$^4$ and R$^5$ are hydrogen. Especially preferred groups of R$^3$ are hydrogen or methyl. Especially preferred groups of R$^6$ are hydrogen, hydroxy or phenyl. Especially preferred groups of A are 4-OCH$_2$, 5-OCH$_2$, 7-OCH$_2$, 4-NHCH$_2$ and 4-OCH$_2$CH$_2$. An especially preferred compound according to the invention is 4-benzyloxy-2-methylbenzimidazole.

Illustrative examples of compounds included in the scope of the invention are given in the examples and in the following Table 1.

TABLE 1

Illustrative examples of compounds included in the scope of the invention

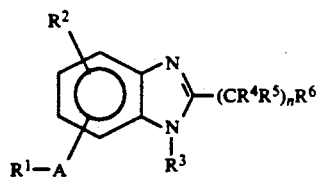

| R$^3$ | (CR$^4$R$^5$)$_n$R$^6$ | R$^2$ | A—R$^1$ |
|---|---|---|---|
| H | H | H | 4-OCH$_2$—⌬ |

TABLE 1-continued
Illustrative examples of compounds included in the scope of the invention
| R³ | (CR⁴R⁵)ₙR⁶ | R² | A—R¹ |
|---|---|---|---|
| H | CH₃ | H | 4-OCH₂—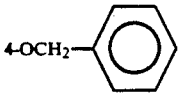 |
| H | CH₂CH₃ | H | 4-OCH₂—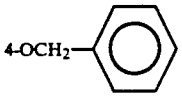 |
| CH₃ | CH₃ | H | 4-OCH₂—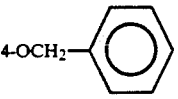 |
| CH₃ | CH₃ | H | 7-OCH₂—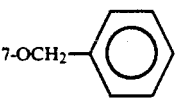 |
| H | CH₃ | H | 5-OCH₂—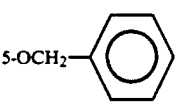 |
| H | CH₃ | H | 4-NHCH₂—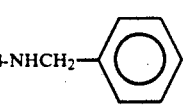 |
| H | CH₃ | H | 4-OCH₂CH₂—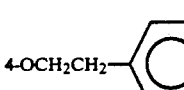 |
| H | CH(CH₃)₂ | H | 4-OCH₂—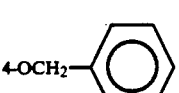 |
| H | CH₂—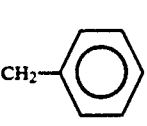 | H | 4-OCH₂—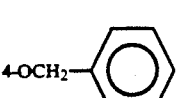 |
| CH₂CH₃ | CH₃ | H | 4-OCH₂—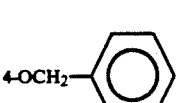 |
| CH(CH₃)₂ | CH₃ | H | 7-CH₂CH₂—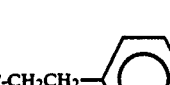 |

TABLE 1-continued
Illustrative examples of compounds included in the scope of the invention
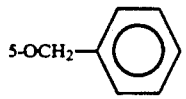
| R³ | (CR⁴R⁵)ₙR⁶ | R² | A—R¹ |
|---|---|---|---|
| H | H | H | 5-OCH₂—<phenyl> |
| H | CH₃ | H | 4-CH₂O—<phenyl> |
| H | CH₃ | H | 5-OCH₂CH₂CH₂—<phenyl> |
| H | CH₃ | H | 4-OCH₂—<thiophene> |
| H | CH₃ | H | 4-OCH₂—<phenyl>—Cl |
| H | CH₃ | H | 4-OCH₂—<phenyl>—F |
| H | CH₃ | H | 4-OCH₂—<phenyl>—Br |
| H | CH₃ | H | 4-OCH₂—<phenyl>—CH₃ |
| H | CH₃ | H | 4-OCH₂—<phenyl>—OCH₃ |
| H | CH₂OH | H | 4-OCH₂—<phenyl> |
| H | CH₃ | H | 4-OCH₂—<phenyl with F> |

TABLE 1-continued
Illustrative examples of compounds included in the scope of the invention
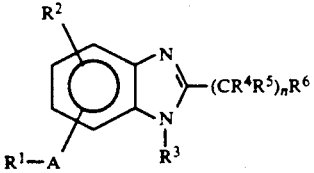
| R³ | (CR⁴R⁵)ₙR⁶ | R² | A—R¹ |
|---|---|---|---|
| H | CH₃ | H | 4-OCH₂—C₆H₄—F |
| H | CH₃ | H | 4-OCH₂—C₆H₃(F)₂ (2,4-difluoro) |
| H | CH₃ | H | 4-OCH₂—C₆H₃(Cl)₂ (3,4-dichloro) |
| H | CH₃ | H | 4-OCH₂—C₆H₃(CH₃)(OCH₃) |
| H | CH₃ | H | 4-OCH₂—C₆H₃(Cl)₂ (2,4-dichloro) |
| H | CH₃ | H | 4-OCH₂—C₆H₂(Cl)(OCH₃)(CH₃) |
| H | CH₃ | H | 4-OCH₂—(2-furyl) |
| H | CH₃ | H | 4-OCH₂—(2-pyridyl) |
| H | CH₃ | H | 4-OCH₂—(3-pyridyl) |
| H | CH₃ | H | 4-OCH₂—(4-pyridyl) |

TABLE 1-continued

Illustrative examples of compounds included in the scope of the invention

[Structure: benzimidazole core with R² at position 5, R¹–A at position 7, R³ on N, and –(CR⁴R⁵)ₙR⁶ at position 2]

| R³ | (CR⁴R⁵)ₙR⁶ | R² | A—R¹ |
|---|---|---|---|
| H | CH₃ | H | 4-OCH₂–(imidazole, NH) |
| H | CH₃ | H | 4-OCH₂–(pyrazine) |
| H | CH₃ | H | 4-OCH₂–(pyrimidine) |
| H | CH₃ | H | 4-OCH₂–(thiophene) |
| H | CH₃ | H | 4-OCH₂–(2-methylimidazole, NH) |
| H | CH₃ | H | 4-OCH₂–(2-methylpyrazine) |
| H | pyridyl | H | 4-OCH₂–phenyl |
| H | CH₃ | 4-CH₃ | 7-OCH₂–phenyl |
| H | CH₃ | 4-Cl | 7-OCH₂–(4-F-phenyl) |
| H | CH₃ | 5-OCH₃ | 7-OCH₂–phenyl |
| H | CH₂CH₃ | 6-Br | 7-OCH₂–phenyl |

TABLE 1-continued

Illustrative examples of compounds included in the scope of the invention

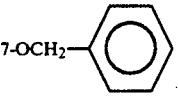

| R³ | (CR⁴R⁵)ₙR⁶ | R² | A—R¹ |
|---|---|---|---|
| CH₃ | CH₃ | 4-CH₃ | 7-OCH₂—⟨phenyl⟩ |
| CH₃ | CH₃ | 7-CH₃ | 4-OCH₂—⟨phenyl⟩ |
| H | CH₃ | H | 4-OCH₂—⟨naphthyl⟩ |
| H | CH₃ | H | 4-N(CH₃)—CH₂—⟨phenyl⟩ |
| H | CH₃ | H | 4-SCH₂—⟨phenyl⟩ |
| H | CH₃ | H | 4-CH₂OCH₂—⟨phenyl⟩ |
| H | CH₃ | H | 4-CH₂—⟨phenyl⟩—F |
| H | CH₃ | H | 4-CH=CH—⟨phenyl⟩ |
| CH₃ | CH₃ | H | 4-CH₂CH₂CH₂—⟨phenyl⟩ |
| H | CH(CH₃)₂ | H | 4-CH=CHCH₂—⟨phenyl⟩ |
| H | C(CH₃)₃ | 4-Cl | 7-OCH₂—⟨phenyl⟩ |

TABLE 1-continued

Illustrative examples of compounds included in the scope of the invention

[Structure: benzimidazole core with R² at 5-position, (CR⁴R⁵)ₙR⁶ at 2-position, R³ on N1, and R¹–A at 7-position]

| R³ | (CR⁴R⁵)ₙR⁶ | R² | A—R¹ |
|---|---|---|---|
| H | CH₂-(2-thienyl) | 7-CH₃ | 4-OCH₂-phenyl |
| H | CH₂-(2-pyridyl) | H | 4-OCH₂-phenyl |
| H | CH₂-(2-pyridyl) | 4-Br | 7-OCH₂-phenyl |
| H | CH₂-(4-pyridyl) | 7-OCH₃ | 4-OCH₂-phenyl |
| H | CH₂-(2-pyridyl, 5-OCH₃) | H | 4-OCH₂-phenyl |
| H | CH₃ | H | 4-CH₂CH₂S-phenyl |
| H | CH₃ | H | 4-NHCH₂CH₂-phenyl |
| H | 2-imidazolyl (NH) | H | 4-OCH₂-phenyl |
| H | 2-furyl | H | 4-OCH₂-phenyl |
| H | CH₂-(2-pyrazinyl) | H | 4-OCH₂-phenyl |
| H | CH(CH₃)-phenyl | H | 4-OCH₂-phenyl |

TABLE 1-continued
Illustrative examples of compounds included in the scope of the invention
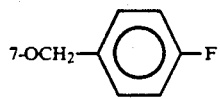
| $R^3$ | $(CR^4R^5)_nR^6$ | $R^2$ | $A-R^1$ |
|---|---|---|---|
| H | CH$_3$ | 4-CH$_3$ | 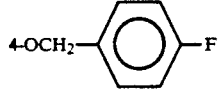 |
| H | CH$_3$ | 7-CH$_3$ | 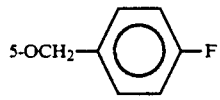 |
| H | CH$_3$ | H | 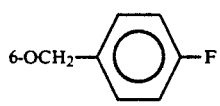 |
| H | CH$_3$ | 5-Cl | 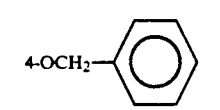 |
| H | NH$_2$ | H | 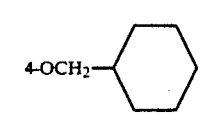 |
| H | CH$_3$ | H | 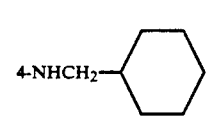 |
| H | CH$_3$ | H | 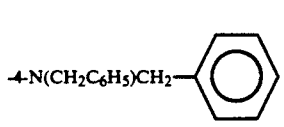 |
| H | CH$_3$ | H | 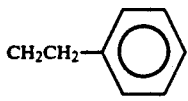 |
| 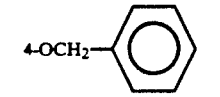 | CH$_3$ | H | 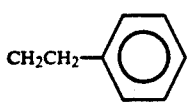 |
| 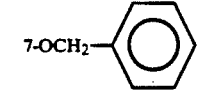 | CH$_3$ | H | 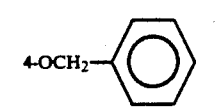 |
| H | N(CH$_3$)$_2$ | H |  |

TABLE 1-continued
Illustrative examples of compounds included in the scope of the invention

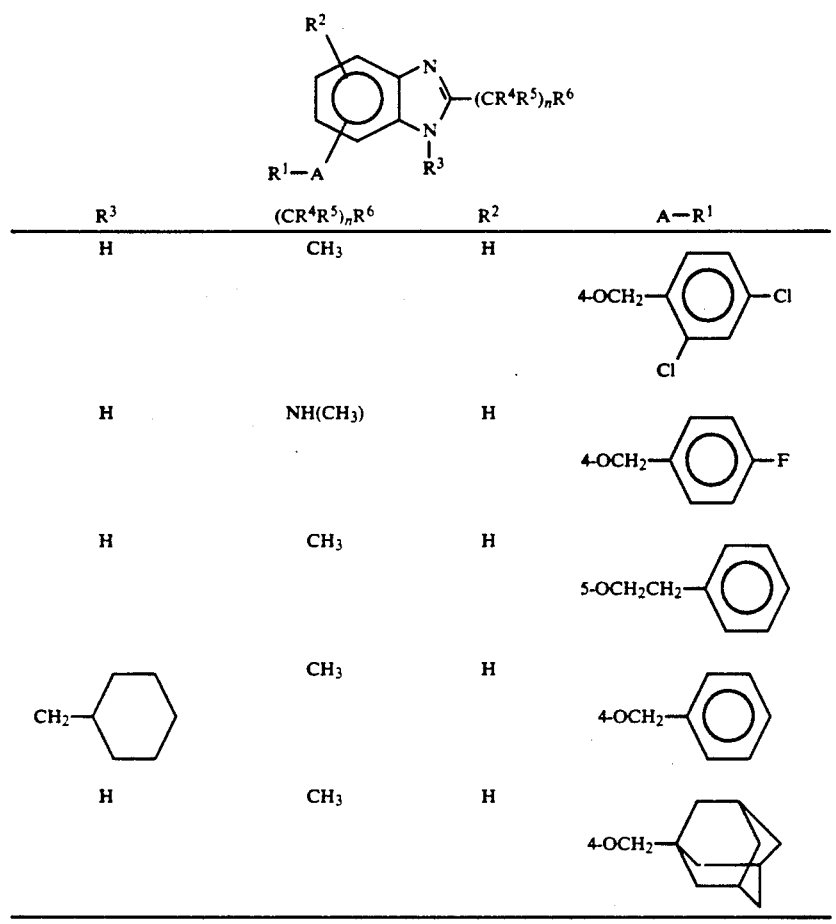

Preparation

The present invention also provides processes for the manufacture of the compounds with the general formula I.

The compounds are prepared in the following way.

A. A Compound of the General Formula II

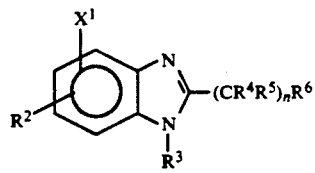

wherein $R^2$, $R^3$, $R^4$, $R^5$ and $R^6$ are as defined above is reacted with a compound of the formula III

wherein $R^1$ is as defined above, $X^1$ is —OH, —SH, or —NHR and $X^2$ is a leaving group, such as a halide, tosyloxy or mesyloxy; and m is an integer 1-6 whereby a compound of the general formula I, wherein $R^1$, $R^2$, $R^3$, $R^4$, $R^5$, $R^6$ and n are as defined above and A is —O(CH$_2$)$_m$, —S(CH$_2$)$_m$ or —NR(CH$_2$)$_m$ is obtained.

It is convenient to conduct this reaction in the presence of a base. The base is e.g. an alkali metal hydroxide, such as sodium hydroxide and potassium hydroxide; a sodium alcoholate, such as sodium methoxide and sodium ethoxide; and alkali metal hydride, such as sodium hydride and potassium hydride; an alkali metal carbonate, such as potassium carbonate and sodium carbonate; or an organic amine, such as triethylamine. The solvent used for the reaction is preferably alcohol, e.g. methanol or ethanol, another polar solvent such as dimethylformamide.

The reaction temperature ranges usually from about 0° C. to about the boiling point of the solvent used, more preferably from about 20° C. to about 80° C. The reaction time ranges from about 0.2 to about 24 hours, more preferably from about 0.5 to about 2 hours.

B. A Compound of the General Formula IV

wherein $R^1$ and $R^2$ are as defined above, $R^{10}$ and $R^{10'}$ are the same or different and each is hydrogen, a lower alkyl group having up to 6 carbon atoms or a group or atom convertible to a lower alkyl group with the proviso that when one of $R^{10}$ and $R^{10'}$ is a lower alkyl group or a group or atom convertible to a lower alkyl group the other of $R^{10}$ and $R^{10'}$ is hydrogen is reacted with a compound of the general formula V $$R^6(CR^4R^5)_nCOR^{11} \qquad V$$

wherein $R^4$, $R^5$, $R^6$ and n are as defined above and $R^{11}$ is a leaving group such as halide, hydroxy, alkoxy, acyloxy or alkoxycarbonyloxy or hydrogen, whereby a compound of the general formula VI

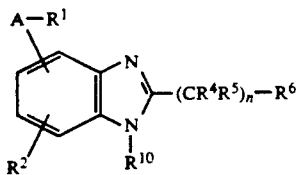

is formed and, if required, a nitrogen atom of the benzimidazole nucleus is alkylated and, if required, protecting groups are removed, to form a compound of the general formula I, and if required, a salt or solvate thereof is formed. The acyloxy, alkoxy and alkoxycarbonyloxy groups in $R^{11}$ have preferably 1-3 carbon atoms.

reaction of a compound of the formula IV with a compound of the formula V is preferably effected by heating with a compound of the general formula V, wherein $R^{11}$ represents a leaving group. For example the compound of the formula V may be an acid, an acid chloride, an acid anhydride, including a mixed anhydride of the acid $R^6(CR^4R^5)_nCOOH$ and a haloformate ester. The presence of an acid catalyst, e.g. HCl, may be necessary.

C. A Compound of the General Formula VII

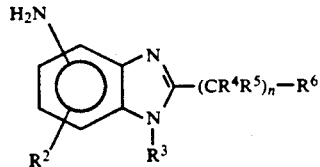

wherein $R^2$, $R^3$, $R^4$, $R^5$ and $R^6$ are as defined above is reacted with a compound of the general formula VIII

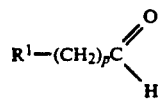

wherein $R^1$ is as defined above and p is an integer 0-5 to form a compound of the general formula IX

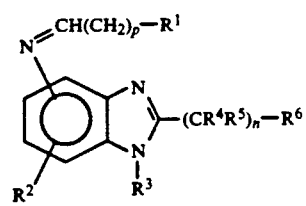

wherein $R^1$, $R^2$, $R^3$, $R^4$, $R^5$ and $R^6$ are as defined above and whereafter the compound of the formula IX is hydrogenated to a compound of the general formula I, wherein A is $-NR(CH_2)_m-$ and $R^1$, $R^2$, $R^3$, $R^4$, $R^5$, $R^6$, n and m are as defined above.

EXAMPLES

Example 1

Preparation of 4-benzyloxybenzimidazole

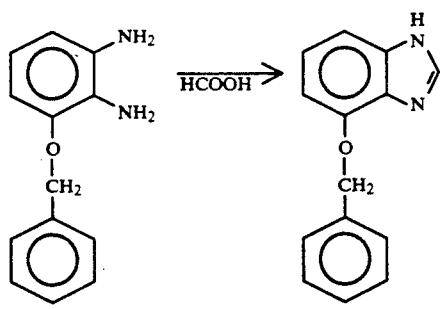

A mixture of 3-benzyloxy-1,2-diaminobenzene 1.6 g (0.0073 mol) and formic acid (2.6 g, 0.057 mol) was heated to reflux for 1.5 h. The resulting mixture was then cooled, dissolved in methylene chloride, washed with 10% sodium carbonate solution, dried ($Na_2SO_4$) and evaporated to dryness in vacuo. The residue was recrystallized from acetonitrile to give the title compound in 0.75 g (46%) yield, m.p. 165°–167° C.

Example 2

Preparation of 4-benzyloxy-2-methylbenzimidazole

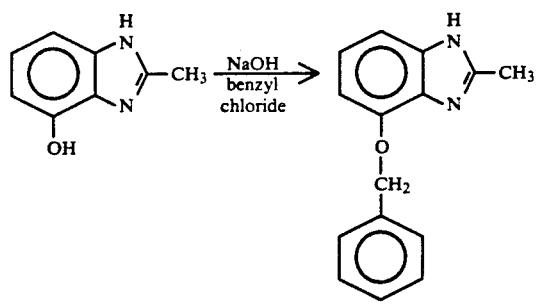

To a stirred solution of 7.3 g (0.049 mol) 4-hydroxy-2-methylbenzimidazole in 300 ml ethanol at ambient temperature 2.0 g (0.049 mol) NaOH in 4 ml water was added dropwise. The solution was stirred for 10 min and 6.3 g (0.049 mol) benzyl chloride was then added dropwise.

The reaction mixture was heated under reflux for 20 h. Upon cooling to ambient temperature the volatiles were removed under reduced pressure. The residue obtained was dissolved in methylene chloride, washed with water and dried ($Na_2SO_4$). Following filtration, methylene chloride was removed under reduced pressure to give an oil. Chromatography on silica gel and elution with methylene chloride:methanol (10:1) gave 4.3 g (0.018 mol), yield: 37% of 4-benzyloxy-2-methylbenzimidazole m.p. 119°–121° C.

Examples 3–8

In the same manner as described above the following compounds were obtained.

4-benzyloxy-2-ethylbenzimidazole
mp: 78°–80° C.

yield: 33%
5-benzyloxy-2-methylbenzimidazole
mp: 164°-165° C.
yield 17%
4-(p-chlorobenzyloxy)-2-methylbenzimidazole
mp: 230°-231° C.
yield: 7%
4-(p-fluorobenzyloxy)-2-methylbenzimidazole
mp 203°-205° C.
yield: 22%
4-benzyloxy-2-hydroxymethylbenzimidazole
mp: 146°-147° C.
yield: 3%
2-methyl-4-phenylethoxybenzimidazole
mp: 176°-178° C.
yield: 15%

Example 9

Preparation of 4-benzylamino-2-methylbenzimidazole

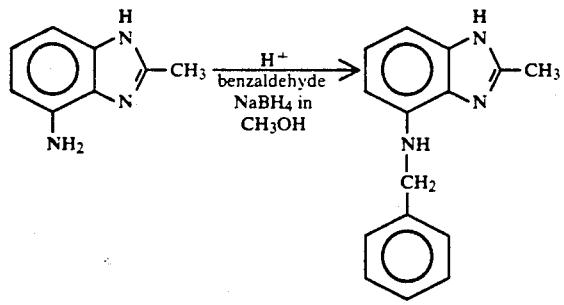

A mixture of 3.8 g (0.026 mol) 4-amino-2-methylbenzimidazole, 2.7 g (0.026 mol) benzaldehyde and 0.05 g paratoluene sulfonic acid in 250 ml toluene was refluxed and the water formed was separated during 20 h. Upon cooling the volatiles were removed under reduced pressure. The residue obtained was suspended in 150 ml methanol and 1.8 g (0.048 mol) NaBH$_4$ was added. The mixture was stirred at room temperature for 2 h and methanol was removed under reduced pressure. The residue was dissolved in methylene chloride, washed with water and dried (Na$_2$SO$_4$). After filtration, methylene chloride was removed under reduced pressure. Chromatography on silica gel and elution with methylene chloride:methanol (10:1) gave 0.1 g (0.00042 mol) of 4-benzylamino-2-methyl benzimidazole NMR δ (CDCl$_3$) 2.45 (s, 3H), 4.40 (s, 2H), 6.30 (dd, 1H), 6.70 (dd,1H), 6.95 (dd,1H), 6.95 (dd,1H), 7.05-7.40 (m,5H).

Example 10

Preparation of 4-benzyloxy-1,2-dimethylbenzimidazole and 7-benzyloxy-1,2-dimethylbenzimidazole

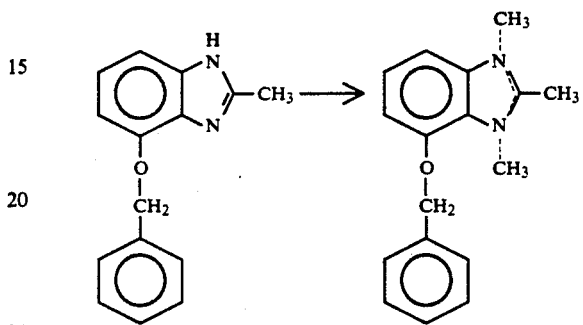

To a mixture of 0.5 g (0.021 mol) 4-benzyloxy-2-methylbenzimidazole 0.71 g (0.021 mol) tetrabutylammonium hydrogen sulfate and 0.48 g (0.0033 mol) methyl iodide in 30 ml methylene chloride and 0.17 g (0.0042 mol) NaOH in 30 ml H$_2$O was added dropwise with stirring. The mixture was heated to reflux for 2 h. Upon cooling the organic layer was separated and the volatiles were removed under reduced pressure to give an oil. The oil was suspended in ether, tetrabutylammonium iodide was filtered off and the volatiles were removed. Chromatography on silica gel and elution with methylene chloride methanol (10:1) gave 0.24 g (0.00095 mol) yield: 45% of the isomeric product 4-benzyloxy-1,2-dimethylbenzimidazole and 7-benzyloxy-1,2-dimethylbenzimidazole mp: 100°-101° C.

The compounds 11-24 listed in the following Table 2 were prepared according to process A or B.

TABLE 2

Summary of Examples 1-10

| Process for prep. | Ex. No. | A | R$^1$ | R$^2$ | R$^3$ | R$^4$ | R$^5$ | R$^6$ | n | yield % | Identifying data |
|---|---|---|---|---|---|---|---|---|---|---|---|
| B | 1 | 4-O—CH$_2$ | phenyl | H | H | H | H | H | 0 | 46 | 165-167° C. |
| A | 2 | 4-O—CH$_2$ | phenyl | H | H | H | H | H | 1 | 37 | 119-121° C. |
|   | 3 | 4-O—CH$_2$ | phenyl | H | H | H | H | H | 2 | 33 | 78-80° C. |
|   | 4 | 5-O—CH$_2$ | phenyl | H | H | H | H | H | 1 | 17 | 164-165° C. |
|   | 5 | 4-O—CH$_2$ | 4'-Cl-phenyl | H | H | H | H | H | 1 | 7 | 230-231° C. |
|   | 6 | 4-O—CH$_2$ | 4'-F-phenyl | H | H | H | H | H | 1 | 22 | 203-205° C. |
|   | 7 | 4-O—CH$_2$ | phenyl | H | H | H | H | OH | 1 | 3 | 146-147° C. |
|   | 8 | 4-O—CH$_2$CH$_2$ | phenyl | H | H | H | H | H | 1 | 15 | 176-178° C. |
| C | 9 | 4-NH—CH$_2$ | phenyl | H | H | H | H | H | 1 | 2 | NMR |
|   | 10 | { 4-O—CH$_2$ / 7-OCH$_2$ | phenyl | H | CH$_3$ | H | H | H | 1 | 45 | 100-101 (isomeric mixture) |
|   |    |                          | phenyl | H | CH$_3$ | H | H | H | 1 |    |                           |
| B | 11 | 4-OCH$_2$ | phenyl | H | H | H | H | phenyl | 1 | 2 | NMR |
| B | 12 | 4-OCH$_2$ | 2',4'-di-Cl-phenyl | H | H | H | H | H | 1 | 33 | 205-207° C. |
| B | 13 | 4-OCH$_2$ | 2',4'-di-F-phenyl | H | H | H | H | H | 1 | 27 | 190-192° C. |
| B | 14 | 5-OCH$_2$ | 4'-F-phenyl | H | H | H | H | H | 1 | 9 | 79-80° C. |
| A | 15 | 4-OCH$_2$ | (thiophene) | H | H | H | H | H | 1 | 2 | 155-156° C. |
| A | 16 | 4-OCH$_2$ | 3'-F-phenyl | H | H | H | H | H | 1 | 18 | 140° C. (HCl salt) |

TABLE 2-continued
Summary of Examples 1-10

| Process for prep. | Ex. No. | A | $R^1$ | $R^2$ | $R^3$ | $R^4$ | $R^5$ | $R^6$ | n | yield % | Identifying data |
|---|---|---|---|---|---|---|---|---|---|---|---|
| B | 17 | 4-OCH$_2$ | 2'-F-phenyl | H | H | H | H | H | 1 | 23 | 148° C. |
| A | 18 | 4-OCH$_2$ | phenyl | — | H | — | — | NH$_2$ | 0 | 13 | NMR |
| A | 19 | 4-OCH$_2$ | cyklohexyl | H | H | H | H | H | 1 | 23 | 128–130° C. |
| A | 20 | 4-NHCH$_2$ | cyklohexyl | H | H | H | H | H | 1 | 2 | 90° C. |
| A | 21 | 4-N(CH$_2$—C$_6$H$_5$)CH$_2$ | phenyl | H | H | H | H | H | 1 | 11 | NMR |
| A | 22 | 4-OCH$_2$ | phenyl | H | CH$_2$CH$_2$—C$_6$H$_5$ | H | H | H | 1 | 6 | (isomeric mixture) NMR |
| | | 7-OCH$_2$ | phenyl | H | CH$_2$CH$_2$—C$_6$H$_5$ | H | H | H | 1 | | |
| A | 23 | 4-OCH$_2$ | phenyl | H | H | H | H | N(CH$_3$)$_2$ | 0 | 20 | 208° C. |
| B | 24 | 5-OCH$_2$CH$_2$ | phenyl | H | H | H | H | H | 1 | 25 | 139° C. |

$^1$H NMR-data for compounds 11, 18, 21 and 22 are given in the following Table 3.

TABLE 3

| Compound No. | Solvent | $^1$H NMR NMR δ |
|---|---|---|
| 11 | CDCl$_3$ | 4.0 (s, 2H), 5.15 (s, 2H), 6.75 (d, 1H), 7.0–7.4 (m, 7H) |
| 18 | CD$_3$OD | 5.25 (s, 2H), 6.8 (d, 1H), 7.05 (t, 1H), 7.35–7.45 (m, 3H), 7.6 (d, 2H) |
| 21 | DMSO | 2.45 (s, 3H), 4.9 (s, 4H), 6.25 (d, 1H), J = 8 Hz, 6.8 (m, 2H), 7.2 (m, 2H), 7.25 (s(broad), 8H) |
| 22 | CDCl$_3$ | 2.15 (s, 3H), 2.25 (s, 3H), 3.0 (t, 2H), 3.1 (t, 2H), 4.3 (t, 2H), 4.45 (t, 2H), 5.25 (s, 2H), 5.35 (s, 2H), 6.7 (d, 1H), 6.75 (dd, 2H), 6.85 (d, 1H), 6.9 (d, 1H), 7.0 (dd, 2H) 7.1–7.2 (m, 5H), 7.25–7.4 (m, 10H), 7.5–7.6 (m, 4H) |

The following examples illustrate intermediates useful in the preparation of the compounds exemplified in Examples 1-10 and Table 1.

Example I

Preparation of 2,3-diaminophenol

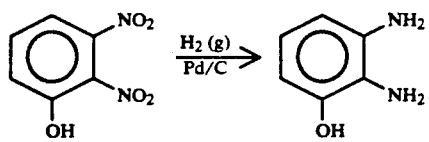

2,3-dinitrophenol (80%) 25 g (0.11 mol) was dissolved in 700 ml ethanol and 0.5 g Pd/C was added. The mixture was hydrogenated at room temperature until the uptake of hydrogen ceased (4 h). The solution was filtered (celite) in N$_2$-atmosphere and evaporated to dryness in vacuo to give the title compound as an unstable oil (18 g), which was used immediately for the next step.

Example II

Preparation of 2,3-diacetamidophenol

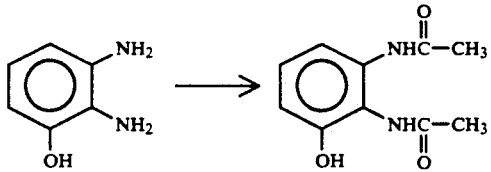

To 18 g (0.11 mol) 2,3-diaminophenol obtained according to Example I 38 ml (0.40 mol) of acetic anhydride was added. The mixture was stirred for 45 min and 50 ml ice and water were added. After stirring for 30 min the product was filtered off and dried to give (15.8 g) of the title compound.

Example III

Preparation of 4-hydroxy-2-methylbenzimidazole

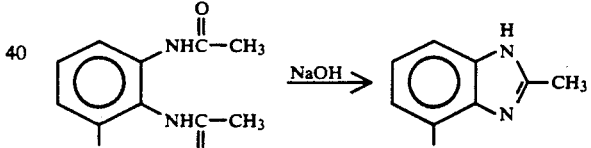

To a solution of 6.8M NaOH 15.8 g (0.076 mol) of 2,3-diacetamidophenol was added and the mixture was heated under reflux for 2 h. Upon cooling the pH of the solution was adjusted to 8.5 with 2M HCl. The solid was filtered off, washed with water and dried to give 7.6 g of the title compound.

Example IV

Preparation of 4-hydroxy-2-hydroxymethylbenzimidazole

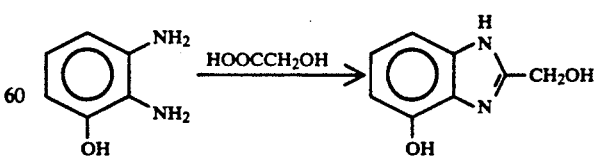

To a solution of 40 ml 4M CHl 1.1 g (0.0087 mol) of 2,3-diaminophenol and 2 g (0.026 mol) of glycolic acid were added and the solution was heated under reflux for 20 h. Upon cooling the reaction mixture was alkalized with 10M NaOH to pH 8.5. The volatiles were removed under reduced pressure and the residual oil was suspended in methanol. The suspension was filtered and evaporated to dryness in vacuo. Chromatography on silica gel and elution with methylene chloride:methanol (10:2) gave 0.78 g of the title compound.

Example V

Preparation of 3-benzyloxy-1,2-diaminobenzene

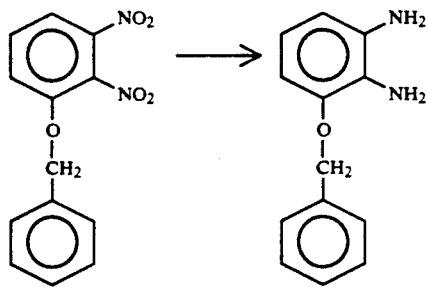

To a solution of 3-benzyloxy-1,2-dinitrobenzene (2 g, 0.0073 mol) in 300 ml ethanol Raney-nickel (1 g) was added and the mixture was hydrogenated at room temperature and atmospheric pressure until the uptake of hydrogen ceased (30 min). The colourless solution was filtered (celite) and evaporated to dryness in vacuo to give the title compound as an unstable oil (1.6 g) which was used immediately for the next step.

For clinical use the compounds of the invention are formulated into pharmaceutical formulations for oral, rectal, parenteral or other mode of administration. The pharmaceutical formulation contains compound of the invention in combination with a pharmaceutically acceptable carrier. The carrier may be in the form of a solid, semi-solid or liquid diluent, or a capsule. These pharmaceutical preparations are a further object of the invention. Usually the amount of active compounds is between 0.1-95% by weight of the preparation, between 0.2-20% by weight in preparations for parenteral use and between 1 and 50% by weight in preparations for oral administration.

In the preparation of pharmaceutical formulations containing a compound of the present invention in the form of dosage units for oral administration the compound selected may be mixed with a solid, powdered carrier, such as lactose, saccharose, sorbitol, mannitol, starch, amylopectin, cellulose derivatives, gelatin, or another suitable carrier, as well as with lubricating agents such as magnesium stearate, calcium stearate, sodium steryl fumarate and polyethylene glycol waxes. The mixture is then processed into granules or pressed into tablets. An enteric coating which protects the active compound from acid degradation as long as the dosage form remains in the stomach may wanted. The enteric coating is chosen among pharmaceutically acceptable enteric-coating materials e.g. beeswax, shellac or anionic film-forming polymers such as cellulose acetate phthalate, hydroxypropylmethylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

Soft gelatine capsules may be prepared with capsules containing a mixture of the active compound or compounds of the invention, vegetable oil, fat, or other suitable vehicle for soft gelatine capsules. Soft gelatine capsules may also be enteric coated as described above. Hard gelatine capsules may contain granules or enteric-coated granules of the active compound. Hard gelatine capsules may also contain the active compound in combination with a solid powdered carrier such as lactose, saccharose, sorbitol, mannitol, potato starch, corn starch, amylopectin, cellulose derivatives or gelatine. The hard gelatine capsules may be enteric coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugaralcohols and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to by reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 500 mg per day of active substance.

Pharmaceutical preparations containing a compound of the invention as active ingredient are illustrated in the following examples.

Example 11

Syrup

A syrup containing 1% (weight per volume) of active substance was prepared from the following ingredients:

| | |
|---|---|
| 4-Benzyloxy-2-methylbenzimidazole | 1.0 g |
| Sugar, powder | 30.0 g |
| Saccharine | 0.6 g |
| Glycerol | 5.0 g |
| Flavouring agent | 0.05 g |
| Ethanol 96% | 5.0 g |
| Distilled water q.s to a final volume of | 100 ml |

Sugar and saccharine were dissolved in 60 g of warm water. After cooling the acid addition salt was dissolved in the sugar solution and glycerol and a solution of flavouring agents dissolved in ethanol were added. The mixture was diluted with water to a final volume of 100 ml.

The above given active substance may be replaced with other pharmaceutically acceptable acid addition salts.

Example 12

Enteric-coated tablets

An enteric-coated tablet containing 20 mg of active compound was prepared from the following ingredients:

| I 4-(p-Fluorobenzyloxy)-2-methyl-benzimidazole | 200 g |
|---|---|
| Lactose | 700 g |
| Methyl cellulose | 6 g |
| Polyvinylpyrrolidone cross-linked | 50 g |
| Magnesium stearate | 15 g |
| Sodium carbonate | 6 g |
| Distilled water | q.s. |
| II Cellulose acetate phthalate | 200 g |
| Cetyl alcohol | 15 g |
| Isopropanol | 2000 g |
| Methylene chloride | 2000 g |

I   4-(p-Fluorobenzyloxy)-2-methyl-benzimidazole, powder, was mixed with lactose and cross-linked polyvinylpyrrolidone and granulated with a water solution of methyl cellulose and sodium carbonate. The wet mass was forced through a sieve and the granulate dried in an oven. After drying the granulate was mixed with magnesium stearate. The dry mixture was pressed into tablet cores (10,000 tablets), each tablet containing 20 mg of active substance, in a tabletting machine using 6 mm diameter punches.

II A solution of cellulose acetate phthalate and cetyl alcohol in isopropanol/methylene chloride was sprayed onto the tablets I in an ACCELA COTA ®, Manesty coating equipment. A final tablet weight of 110 mg was obtained.

Example 13

Solution for Intravenous Administration

A parenteral formulation for intravenous use, containing 4 mg of active compound per ml, was prepared from the following ingredients:

| 4-(p-Chlorobenzyloxy)-2-methylbenzimidazole | 4 g |
|---|---|
| Polyethylene glycol 400 for injection | 400 g |
| Disodium hydrogen phosphate | q.s. |
| Sterile water to a final volume of | 1000 ml |

4-p-Chlorobenzyloxy)-2-methylbenzimidazole was dissolved in polyethylene glycol 400 and 550 ml of water was added. pH of the solution was brought to pH 7.4 by adding a water solution of disodium hydrogen phosphate and water was added to a final volume of 1000 ml. The solution was filtered through a 0.22 μm filter and immediately dispensed into 10 ml sterile ampoules. The ampoules were sealed.

We claim:

1. A compound of the formula I

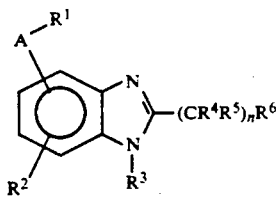

or a pharmaceutically acceptable salt or solvate thereof, in which $R^1$ represents a substituted or unsubstituted aryl other than pyridine or pyrimidine or cykloalkyl group with 3-8 carbon atoms in the unsubstituted cyclic group; or an adamantyl group;

$R^2$ represents hydrogen, a lower alkyl, a lower alkoxy or halogen;

$R^3$ represents hydrogen, a lower alkyl, a phenylalkyl with 1-4 carbon atoms in the alkyl group or a cycloalkyl-alkyl group with 3-8 carbon atoms in the cyclic group and 1-4 carbon atoms in the alkyl group;

n is an integer 0-6

$R^4$ represents hydrogen or a lower alkyl;

$R^5$ represents hydrogen or a lower alkyl;

$R^6$ represents hydrogen, a lower alkyl, a substituted or unsubstituted aryl group or when n is 1-6 a hydroxyl group or when n is 0 an amino, an alkylamino or a dialkylamino group with 1-4 carbon atoms in the alkyl groups;

A represents an alkylene, optionally connected to, or interrupted by an optionally substituted hetero atom selected from O, S, and NR, wherein R is hydrogen, a lower alkyl, a phenylalkyl with 1-4 carbon atoms in the alkyl group or cycloalkyl-alkyl group with 3-8 carbon atoms in the cyclic group and 1-4 carbon atoms in the alkyl group; or an alkenylene with the provisos that when a) n is 0 and $R^2$, $R^3$ and $R^6$ are all hydrogen, then the group $A$-$R^1$ is not 7-benzylamino or 7-(4'-methoxy)-benzylamino; and when b) n is 1 and $R^3$, $R^4$ and $R^5$ are all hydrogen, $R^2$ is 4-methyl, $R^6$ is ethyl, phenyl, benzyl, or (4'-methoxy)-phenyl then the group $A$-$R^1$ is not 7-benzyloxy; and when c) n is 0, $R^2$ is 4-methyl, $R^3$ is hydrogen and $R^6$ is phenyl, then the group $A$-$R^1$ is not 7-benzyloxy.

2. A compound of the formula I according to claim 1 wherein $R^1$ represents a substituted or unsubstituted aryl group of the formula II

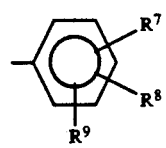

in which each of $R^7$, $R^8$, $R^9$ independently represents hydrogen, a lower alkyl having up to 6 carbon atoms, a lower alkoxy having up to 6 carbon atoms, halogen, preferably chloro or fluoro, or a heterocyclic aryl group of one of the following formulas

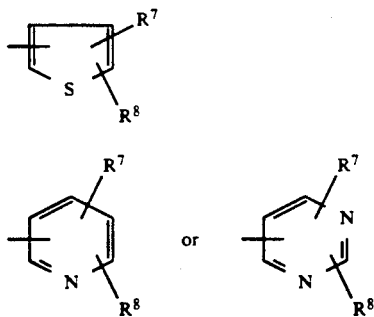

in which $R^7$ and $R^8$ have the meanings given above;

$R^2$ represents hydrogen, a lower alkyl with 1–6 carbon atoms, a lower alkoxy with 1–6 carbon atoms, chloro, bromo or fluoro;

$R^3$, $R^4$ and $R^5$ are the same or different and represent hydrogen or a lower alkyl with 1–6 carbon atoms;

$R^6$ represents hydrogen, a lower alkyl with 1–6 carbon atoms, a hydroxyl group or a substituted or unsubstituted aryl group as defined above for $R^1$, whereby $R^1$ and $R^6$ are the same or different;

n is an integer 0–6;

A represents an alkylene with up to 6 carbon atoms, optionally connected to or interrupted by an eventually substituted hetero atom selected from O, S and NR, wherein R is hydrogen or a lower alkyl with 1–6 carbon atoms; or an alkenylene with up to 6 carbon atoms.

3. A compound according to claim 1 wherein A is —O—CH$_2$—, $R^1$ is phenyl, $R^2$, $R^3$, $R^4$, $R^5$ and $R^6$ are all hydrogen and n is 1.

4. A compound according to claim 1 wherein A is —O—CH$_2$—, $R^1$ is phenyl, $R^3$ is methyl, $R^2$, $R^4$, $R^5$ and $R^6$ are all hydrogen and n is 1.

5. A pharmaceutical composition containing as active ingredient a compound according to claim 1, together with a pharmaceutically acceptable carrier.

6. A method for inhibiting gastric acid secretion which comprises administering to mammals an effective amount of a compound of the formula I

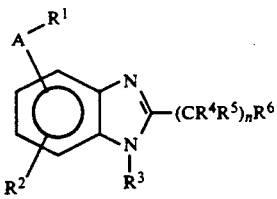

or a pharmaceutically acceptable salt or solvate thereof, in which $R^1$ represents a substituted or unsubstituted aryl other than pyridine or pyrimidine or cykloalkyl group with 3–8 carbon atoms in the unsubstituted cyclic group; or an adamantyl group;

$R^2$ represents hydrogen, a lower alkyl, a lower alkoxy or halogen;

$R^3$ represents hydrogen, a lower alkyl, a phenylalkyl with 1–4 carbon atoms in the alkyl group or a cycloalkyl-alkyl group with 3–8 carbon atoms in the cyclic group and 1–4 carbon atoms in the alkyl group;

n is an integer 0–6

$R^4$ represents hydrogen or a lower alkyl;

$R^5$ represents hydrogen or a lower alkyl;

$R^6$ represents hydrogen, a lower alkyl, a substituted or unsubstituted aryl group or when n is 1–6 a hydroxyl group or when n is 0 an amino, an alkylamino or a dialkylamino group with 1–4 carbon atoms in the alkyl groups;

A represents an alkylene, optionally connected to, or interrupted by an optionally substituted hetero atom selected from O, S, and NR, wherein R is hydrogen, a lower alkyl, a phenylalkyl with 1–4 carbon atoms in the alkyl group or cycloalkyl-alkyl group with 3–8 carbon atoms in the cyclic group and 1–4 carbon atoms in the alkyl group; or an alkenylene.

7. A method for the treatment of gastrointestinal inflammatory diseases in mammals which comprises administering an effective amount of a compound as defined in claim 6.

* * * * *

UNITED STATES PATENT AND TRADEMARK OFFICE
CERTIFICATE OF CORRECTION

PATENT NO. : 5,106,862
DATED : April 21, 1992
INVENTOR(S) : Briving et. al.

It is certified that error appears in the above-indentified patent and that said Letters Patent is hereby corrected as shown below:

Col. 21, line 27, before "reaction," insert -- The --;

Col. 27, line 55, after "may " insert -- be --;

Col. 31, lines 8-14, change the formulas

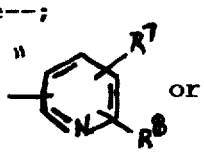 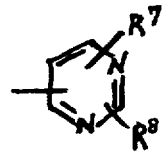

to -- 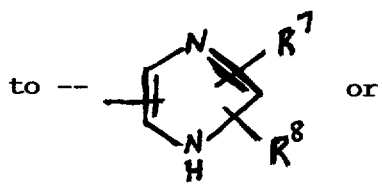 or 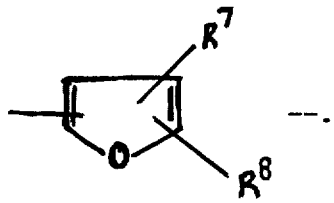 --.

Signed and Sealed this

Third Day of February, 1998

Attest:

BRUCE LEHMAN

Attesting Officer

Commissioner of Patents and Trademarks